United States Patent [19]

Helms et al.

[11] Patent Number: 5,014,010

[45] Date of Patent: May 7, 1991

[54] DUAL FREQUENCY MICROWAVE WATER CUT MONITORING MEANS AND METHOD

[75] Inventors: David A. Helms; Michael G. Durrett; Gregory J. Hatton, all of Houston, Tex.

[73] Assignee: Texaco Inc., White Plains, N.Y.

[21] Appl. No.: 337,017

[22] Filed: Apr. 10, 1989

[51] Int. Cl.$^5$ ............................................. G01R 27/04
[52] U.S. Cl. ...................... 324/640; 73/73; 374/122
[58] Field of Search .................. 374/122; 324/58.5 A, 324/640, 698

[56] References Cited

U.S. PATENT DOCUMENTS

| | | | |
|---|---|---|---|
| 3,498,112 | 3/1970 | Howard | 73/73 X |
| 4,485,284 | 11/1984 | Pakalis | 73/73 X |
| 4,499,418 | 2/1985 | Helms et al. | 324/58.5 A |
| 4,532,939 | 8/1985 | Yukl | 374/122 X |
| 4,767,982 | 8/1988 | Florig et al. | 324/58.5 A |
| 4,812,734 | 3/1989 | Swanson | 324/640 |

FOREIGN PATENT DOCUMENTS 0960308 12/1974 Canada ......................... 324/58.5 A Primary Examiner—Daniel M. Yasich
Attorney, Agent, or Firm—Robert A. Kulason; James J. o'Loughlin; Ronald G. Gillespie

[57] ABSTRACT

A dual frequency microwave water cut monitor includes a microwave source which provides microwave energies at two different frequencies to a circulator which in turn provides the microwave energies to an antenna. The antenna provides the microwave energies to a petroleum stream and also receives reflected microwave energy back from the stream. The reflected microwave energy is provided by the antenna to the circulator which in turn provides the reflected microwave energies as test microwave energies. A detector assembly connected to the circulator detects the intensities of the test microwave energies and provides a corresponding intensity signal. Indicator apparatus connected to the circulator to the microwave source and to the detector assembly provides an indication of the water cut of the petroleum stream in accordance with the intensity signal and the phase difference between one of the source provided microwave energies and its corresponding test microwave energy.

12 Claims, 1 Drawing Sheet

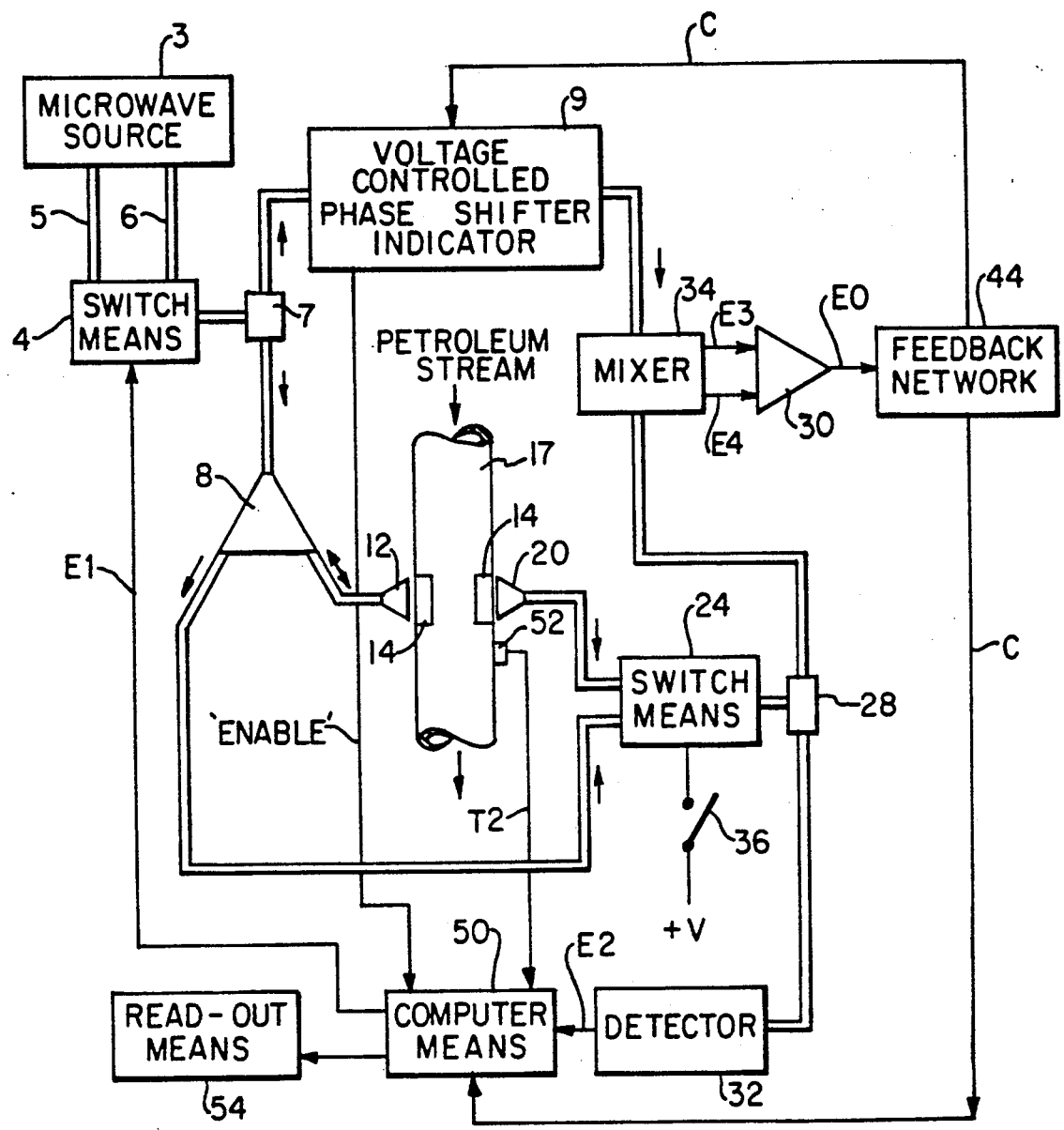

DUAL FREQUENCY MICROWAVE WATER CUT MONITORING MEANS AND METHOD

BACKGROUND OF THE INVENTION

Field of the Invention

The present invention relates to microwave means and methods of monitoring the water cut of a petroleum stream.

SUMMARY OF THE INVENTION

A dual frequency microwave water cut monitor includes a microwave source which provides microwave energies at two different frequencies to a circulator which in turn provides the microwave energies to an antenna. The antenna provides the microwave energies to a petroleum stream and also receives reflected microwave energy back from the stream. The reflected microwave energy is provided by the antenna to the circulator which in turn provides the reflected microwave energies as test microwave energies. A detector assembly connected to the circulator detects the intensities of the test microwave energies and provides a corresponding intensity signal. Indicator apparatus connected to the circulator to the microwave source and to the detector assembly provides an indication of the water cut of the petroleum stream in accordance with the intensity signal and the phase difference between one of the source provided microwave energies and its corresponding test microwave energy.

In another embodiment there is a second antenna which receives microwave energies that has passed through the petroleum stream and provides the received microwave energies as the test microwave energies. The detector assembly is connected to the second antenna and again provides an intensity signal corresponding to the intensities of the test microwave energies. Similarly the indicator apparatus is also connected to the second antenna instead of the circulator and provides the indication of the water cut of the petroleum stream in accordance with the intensity signal and the phase difference between one of the source provided microwave energies and its corresponding test microwave energy.

The objects and advantages of the invention will appear more fully hereinafter, from a consideration of the detailed description which follows, taken together with the accompanying drawings wherein two embodiments are illustrated by way of example. It is to be expressly understood, however, that the drawings are for illustrative purposes only and are not to be construed as defining the limits of the invention.

DESCRIPTION OF THE DRAWING

The drawing is a partial simplified block diagram of a microwave water cut monitor constructed in accordance with the present invention.

DESCRIPTION OF THE INVENTION

The water cut monitor shown in the drawing includes a microwave source 3 providing electromagnetic energies, hereinafter referred to as microwave energy, at two microwave frequencies. Preferred frequencies of 10.119 GHz and 10.369 GHz are used, although the true criteria is that there be a substantial difference between the two frequencies. Source 3 is low powered and may use a microwave gun source. Source 3 provides the microwave energies to switch means 4 via microwave conductors 5 and 6. Switch means 4 is controlled by a signal E1 to pass the microwave energy from either conductor 5 or 6 and provide it to a directional coupler 7. Directional coupler 7 provides the selected microwave energy to a circulator 8 and to a conventional type voltage controlled phase shifter 9. All conductance or carrying of microwave energy is accomplished by using conventional type waveguides.

Circulator 8 provides microwave energy to an antenna 12. Antenna 12 provides the microwave energy through a window 14, which may be made of a conductive ceramic or Teflon, to a petroleum stream having at least oil and water, passing through a pipe 17. Pipe 17 may be a portion of a pipeline having windows 14 or it may be made of the "window" material. The microwave energy provided by antenna 12 passes through the petroleum stream and another window 14 and is received by an antenna 20. Antenna 20 provides the received microwave energy to a switch means 24 which in turn provides the received microwave as test microwave energy to a directional coupler 28, as hereinafter explained. Directional coupler 28 provides the test microwave energy to a detector 32 and to a mixer 34. Detector 32 provides a signal E2 corresponding to the intensity of the microwave energy received by antenna 20.

The petroleum stream also reflects some of the microwave energy back to antenna 12 which passes back through antenna 12 to circulator 8. Circulator 8 blocks the reflected microwave energy from feeding back to source 3 and provides the reflected microwave energy to switch means 24. Reflected microwave energy becomes more important as the distance between antennas 12 and 20 increases. This is especially true where a large pipeline carrying the petroleum stream is being monitored.

A positive direct current voltage +V is provided to a switch 36 which is connected to switch means 24. With switch 36 open, switch means 24 provides microwave energy from antenna 20 as test microwave energy. When switch 36 is closed, the reflected microwave energy from circulator 8 is provided by switch means 24 as the test microwave energy.

The microwave energy from voltage controlled phase shifter 9, hereinafter called the reference microwave energy, and the test microwave energy from directional coupler 28, are provided to mixer 34 which mixes them to provide two electrical signals E3, E4, representative of the phases of the reference microwave energy and the test microwave energy, respectively.

A differential amplifier 40 provides an output signal E0 in accordance with the difference between signals E3 and E4. Signal E0 is a function of the phase difference between the reference microwave energy and the test microwave energy and is provided to a feedback network 44. Feedback network 44 provides a signal C to voltage control phase shifter 5, controlling the phase of the reference microwave energy, and to a mini-computer means 50. Signal E0, and hence the signal C, decreases in amplitude until there is substantially 90° phase difference between the reference microwave energy and the test microwave energy. Voltage control phase shifter 5 indicates the amount of phase shift required to eliminate the phase difference.

Signal E2 from detector 32 is also provided to computer means 50 which contains within it memory means having data related to temperature and phase and amplitude for various percentages of water cuts that could be encountered in the production stream. It has been discovered that the phase difference for measurements in a fluid stream may exceed 360 degrees under certain circumstances. These circumstances include cases where the dielectric of the stream is large, for example when the percentage of water in the petroleum is large, and when the emulsion is water continuous and in cases where the distance between antennas is large as in the case of using larger pipe 17 of FIG. 1.

In those cases the true phase shift may be the measured phase shift plus some integer multiple of 360 degrees. The present invention resolves this ambiguity by monitoring the petroleum at two substantially different frequencies, the main frequency $f_1$, and a secondary frequency, $f_2$, and using the difference in measured phase shift, (phase 1 − phase 2) at the two frequencies to determine the correct integer multiplier to use when computing the true phase shift. The correct integer is chosen from a table created from knowledge of the frequencies involved. The maximum possible size of the integer that may be resolved is limited by the separation of frequencies $f_1$ and $f_2$. In the present case integer size of up to 40 can be resolved. Reduction of frequency separation would increase the maximum integer size further limited only by resolution of the phase shift measurement.

A temperature sensor 52 sensing the temperature of the petroleum stream in pipe 17 and provides a signal T to computer means 50 representative of the sensed temperature.

Phase Shifter 9 also provides an enable signal to computer means 50 allowing computer means 50 to utilize signals T, C and E2. Computer means 50 also provides signal E1 to switch means 4 so that computer means 50 can correlate signal E2 to a particular frequency. Internally computer means 50 uses the phase shift signal C, signal T and the two amplitude levels of signal E2 to address computer means 50 memory means to select the proper water cut values. Computer means 50 provides signals, corresponding to the selected water cut value, to readout means 54 which may be either digital display means or record means or a combination of the two.

What is claimed is:

1. A petroleum stream microwave water cut monitor comprising:
   temperature sensing means for sensing the temperature of the petroleum stream and providing a temperature signal corresponding thereto,
   source means for providing microwave energies at two different frequencies,
   antenna means for providing the petroleum stream with the microwave energies at the two frequencies and for receiving reflected microwave energies back from the stream,
   circulating means connected to the source means and to the antenna means for providing the microwave energy from the source means to the antenna means for providing the reflected microwave energies from the antenna means as test microwave energies,
   detector means connected to the circulating means for detecting the intensities of the test microwave energies and providing an intensity signal corresponding thereto, and
   indicator means connected to the temperature sensing means, to the circulating means, to the source means and to the detector means for providing an indication of the water cut of the petroleum stream in accordance with the temperature signal, the intensity signal and the phase difference between one of the microwave energies provided by the source means and its corresponding test microwave energy; and
   in which the indicator means includes:
   a voltage controlled phase shifter receiving the microwave energies from said source means for phase shifting the microwave energies from the source means in accordance with a phase shift signal to provide reference microwave energies and to provide an enabling signal when the phase shifting is completed,
   phase shift signal means receiving the reference microwave energies and the test microwave energies for providing the phase shift signal to the phase shifter until there is substantially a 90° phase difference between a reference microwave energy and its corresponding test microwave energy, and
   water cut means connected to the temperature sensing means, to the phase shifter, to the detector means and to the phase shift signal means and responsive to the enabling signal from the phase shifter for determining the water cut of the petroleum stream in accordance with the temperature signal, the intensity signal and one of the phase shifts, and providing water cut signals corresponding thereto.

2. A monitor as described in claim 1 in which the phase shift signal means includes:
   mixer means connected to the phase shifter and to the circulating means for mixing a reference microwave energy from the phase shifter with its corresponding test microwave energy from the circulating means to provide two signals representative of the phases of the mixed microwave energies,
   a differential amplifier connected to the mixer means for providing an output signal in accordance with the difference between the two signals from the mixer means, and
   a feedback network connected to the phase shifter and to the differential amplifier which provides the phase shift signal in accordance with the output signal.

3. A monitor as described in claim 2 in which the indicator means further includes:
   read-out means connected to the computer means for providing a read-out of the determined water-cut in accordance with the water cut signals from the computer means.

4. A petroleum stream microwave water cut monitor comprising:
   temperature sensing means for sensing the temperature of a petroleum stream and providing a signal corresponding thereto,
   source means for providing microwave energies at different frequencies,
   first antenna means connected to the source means for providing the petroleum stream with the microwave energies provided by the source means,
   second antenna means for receiving microwave energies that have passed through the petroleum stream and providing the received microwave energies as test microwave energies,
   detector means connected to the second antenna means for detecting the intensities of the test microwave energies and providing an intensity signal corresponding thereto, and indicator means connected to the temperature sensing means, to the second antenna means, to the source means and to the detector means for providing an indication of the water cut of the petroleum stream in accordance with the temperature signal, and intensity signal and the phase difference between one of the microwave energies provided by the source means and its corresponding test microwave energy; and in which the indicator means includes:

a voltage controlled phase shifter receiving the microwave energies from said source means for phase shifting the microwave energies from the source means in accordance with a phase shift signal to provides reference microwave energies and to provide an enabling signal when the phase shifting is completed, phase shift signal means receiving the reference microwave energy and the test microwave energy for providing the phase shift signal to the phase shifter until there is substantially a 90° phase difference between a reference microwave energy and its corresponding test microwave energy, and water cut means connected to the temperature sensing means, to the phase shifter, to the detector means and to the phase shift signal means and responsive o the enabling signal from the phase shifter for determining the water cut of the petroleum stream in accordance with the temperature signal, the intensity signal and one of the phase shifts, and providing water cut signals corresponding thereto.

5. A monitor as described in claim 4 in which the phase shift signal means includes:

mixer means connected to the phase shifter and to the second antenna means for mixing a reference microwave energy from the phase shifter in its corresponding test microwave energy from the second antenna means to provide two signals representative of the phases of the mixed microwave energies, a differential amplifier connected to the mixer means for providing an output signal in accordance with the difference between the two signals from the mixer means, and a feedback network connected to the phase shifter and to the differential amplifier which provides the phase shift signal in accordance with the output signal.

6. A monitor as described in claim 5 in which the indicator means further includes:

read-out means connected to the computer means for providing a read-out of the determined water-cut in accordance with the water cut signals from the computer means.

7. A method of monitoring the water cut of a petroleum stream comprising the steps of:

sensing the temperature of a petroleum stream, providing a temperature signal corresponding to the sensed temperature, providing microwave energies at two different frequencies, providing the petroleum stream with the microwave energies at the two frequencies, receiving reflected microwave energies back from the petroleum stream, providing the reflected microwave energies as test microwave energies, detecting the intensities of the test microwave energies, providing an intensity signal corresponding to the detected intensities, and providing an indication of the water cut of the petroleum stream in accordance with the temperature signal, the intensity signal and the phase difference between one of the provided microwave energies and its corresponding test microwave energy; and in which the indication step includes the steps of:

phase shifting the microwave energies from the source means in accordance with a phase shift signal to provide reference microwave energies, providing an enable signal when the phase shifting is completed, providing the phase shift signal until there is substantially a 90° phase difference between a reference microwave energy and its corresponding test microwave energy, determining the water cut of the petroleum stream in accordance with the enable signal, the temperature signal, the intensity signal and one of the phase shift, and providing water cut signals corresponding to the determined water-cut.

8. A method as described in claim 7 in which the phase shift signal step includes:

mixing a reference microwave energy with its corresponding test microwave energy to provide two signals representative of the phases of the mixed microwave energies, providing an output signal in accordance with the difference between the two signals from the mixing step, and providing the phase shift signal in accordance with the output signal.

9. A method as described in claim 8 in which the indication step further includes:

providing a read-out of the determined water-cut in accordance with the water cut signals.

10. A method of monitoring the water cut of a petroleum stream comprising the steps of:

sensing the temperature of a petroleum stream, providing a signal corresponding to the sensed temperature, providing the petroleum stream with microwave energies at different frequencies from a source, receiving microwave energies that has passed through the petroleum stream, detecting the intensities of the test microwave energies, providing an intensity signal corresponding to the detected energies, and providing an indication of the water cut of the petroleum stream in accordance with the temperature signal, the intensity signal and the phase difference between one of the provided microwave energies and its corresponding test microwave energy; and in which the indication step includes:

phase shifting the source provided microwave energies in accordance with a phase shift signal to provide reference microwave energies.

providing an enabling signal phase shifting is completed, providing the phase shift signal until there is substantially a 90° phase difference between a reference microwave energy and its corresponding test microwave energy, and determining the water cut of the petroleum stream in accordance with the temperature signal, the intensity signal and one of the phase shifts, and providing water cut signals corresponding thereto.

11. A method as described in claim 10 in which the phase shifting step includes:

mixing a reference microwave energy with its corresponding test microwave energy from the second antenna means to provide two signals representative of the phases of the mixed microwave energies, providing an output signal in accordance with the difference between the two signals from the mixing step, and providing the phase shift signal in accordance with the output signal.

12. A method as described in claim 11 in which the indication step further includes:

providing a read-out of the determined water-cut in accordance with the water-cut signals.

* * * * *